United States Patent
Desimone et al.

(10) Patent No.: US 6,451,287 B1
(45) Date of Patent: Sep. 17, 2002

(54) FLUORINATED COPOLYMER SURFACTANTS AND USE THEREOF IN AEROSOL COMPOSITIONS

(75) Inventors: Joseph M. Desimone, Chapel Hill; Terri Johnson Carson, Durham; John F. Miller, Raleigh; Sharon Wells, Carrboro, all of NC (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/580,008

(22) Filed: May 26, 2000

(51) Int. Cl.$^7$ .............................. A61K 9/12; C08L 8/00
(52) U.S. Cl. ..................... 424/45; 514/180; 525/283; 521/149; 521/64
(58) Field of Search .................. 521/149, 64; 525/283; 424/45

(56) References Cited

U.S. PATENT DOCUMENTS

| | | |
|---|---|---|
| 4,352,789 A | 10/1982 | Thiel |
| 4,486,572 A * | 12/1984 | Kennedy ................ 525/283 |
| 4,608,401 A | 8/1986 | Martin |
| 4,755,563 A | 7/1988 | West |
| 4,771,086 A | 9/1988 | Martin |
| 5,118,494 A | 6/1992 | Schultz et al. |
| 5,126,123 A | 6/1992 | Johnson |
| 5,312,882 A | 5/1994 | DeSimone et al. |
| 5,320,906 A | 6/1994 | Eley et al. |
| 5,376,359 A | 12/1994 | Johnson |
| 5,382,623 A | 1/1995 | DeSimone et al. |
| 5,451,633 A | 9/1995 | DeSimone et al. |
| 5,492,688 A | 2/1996 | Byron et al. |
| 5,496,901 A | 3/1996 | DeSimone |
| 5,506,317 A | 4/1996 | DeSimone et al. |
| 5,518,731 A | 5/1996 | Meadows |
| 5,589,105 A | 12/1996 | DeSimone et al. |
| 5,639,441 A | 6/1997 | Sievers et al. |
| 5,827,348 A | 10/1998 | Waddell et al. |
| 5,849,265 A | 12/1998 | Li-Bovet et al. |
| 6,013,245 A | 1/2000 | Taylor |
| 6,225,367 B1 * | 5/2001 | Chaouk et al. ........... 521/149 |

FOREIGN PATENT DOCUMENTS

| | | |
|---|---|---|
| EP | 0 372 777 A2 | 6/1990 |
| EP | 0 372 777 B1 | 1/1993 |
| WO | WO 91/11173 | 8/1991 |
| WO | WO 91/14422 | 10/1991 |
| WO | WO 92/00061 | 1/1992 |

OTHER PUBLICATIONS

Commercial Chemical Division/3M, St. Paul, Minn., "Fluorad" Coating Additive FC–430 . . . , 2 pages (1983).

3M Fluorad Fluorosurfactants Selection Guide, "The 3M Fluorad fluorosurfactants advantage: Dramatically reduced surface tension at extremely low concentrations," Mar. 16, 1999.

3M Fluorad Fluorosurfactants history, 3M fluorosurfactants: helping liquid products function more efficiently, Mar. 16, 1999.

Typical Fluorad Fluorosurfactant Products, Fluorad Fluorosurfactant Products Feb. 25, 1999.

* cited by examiner

Primary Examiner—Jose' G. Dees
Assistant Examiner—M. Haghighatian
(74) Attorney, Agent, or Firm—Christopher P. Rogers

(57) ABSTRACT

Amphiphilic fluorinated block copolymers are disclosed which are useful for increasing the dispersability of particles, preferably drug particles, in a fluorine-containing propellant.

16 Claims, 4 Drawing Sheets

A = Lyophilic tail
B = Lyophobic anchor
D = Drug Particle Surface

FLUORINATED COPOLYMER SURFACTANTS AND USE THEREOF IN AEROSOL COMPOSITIONS

BACKGROUND OF THE INVENTION

1. Field of the Invention

This invention relates to novel surfactants, which are particularly useful in dispersing particles in an aerosol composition containing a fluorine-containing propellant. The invention also relates to pharmaceutical aerosol compositions and methods of stabilizing drugs in such compositions using these surfactants.

2. Description of the Related Art

Drugs for treating respiratory and nasal disorders are frequently administered in aerosol formulations through the mouth or nose. See generally P. Byron, *Respiratory Drug Delivery*, CRC Press, Boca Raton, Fla. (1990). One widely used method for dispensing such an aerosol drug formulation involves making a suspension formulation of the drug as a finely divided powder in a liquefied gas known as a propellant. The suspension is stored in a sealed container capable of withstanding the pressure required to maintain the propellant as a liquid. The suspension is dispensed by activation of a dose-metering valve affixed to the container. Further background concerning the use of surfactants in MDI's is discussed in WO 00/00181, which is incorporated herein by reference.

A metering valve may be designed to consistently release a fixed, predetermined amount of the drug formulation upon each activation. As the suspension is forced from a container through the dose-metering valve by the high vapor pressure of the propellant, the propellant rapidly vaporizes, leaving a cloud of very fine particles of the drug formulation. This cloud is usually directed into the body of the patient by a channeling device, e.g., a cylinder-like or cone-like passage, with one of its ends attached to the outlet of the pressurized container, and the other end inserted in the mouth or nose of the patient. Concurrently with the activation of the aerosol dose-metering valve, the patient inhales the drug formulation particles into the lungs or nasal cavity. Systems for dispensing drugs in this way are known as "metered dose inhalers (MDI's)." See Byron, supra at 167–207.

Many materials, including drug formulations, have a tendency to aggregate (also referred to as "flocculate" or "clump-up") when stored as fine particles having dimensions of a few microns in a suspension. For an aerosol delivery system to work properly the aggregation needs to be controlled so as to maximize free volume in the sedimentary layer since this type of arrangement facilitates redispersion of the particles as compared to a more tightly packed arrangement. Further, the suspension should be substantially homogenous throughout the administered dose at the time of activation of the metering valve.

To control aggregation of fine particles and, thereby, to influence the dispersability of the suspension, compounds known as surface active agents, or surfactants, are often used to coat the surfaces of the fine particles and assist in wetting the particles with an aerosol propellant. The use of surfactants in this way to maintain substantially uniform suspensions is said to "stabilize" the suspensions.

For several years, the chlorofluorocarbons (CFC's) gained wide spread acceptance as the propellants of choice for inhalation drug formulations. However, for environmental reasons, there has been a move to replace chlorofluorocarbons with hydrofluorocarbon (HFC) propellants, such as HFC-134A (1,1,1,2-tetrafluoroethane) and HFC-227 (1,1,1,2,3,3,3-heptafluoropropane). When these hydrofluorocarbon propellants are used as a propellant in a pressurized drug delivery system, various technical problems can occur with various drug formulations. It has proven particularly difficult to form stabilized compositions with such propellants. In light of the need to reduce the use of CFC propellants, there is a continuing need for the development of stabilized aerosol formulations containing HFC propellants.

Thiel in U.S. Pat. No. 4,352,789, teaches the use of insoluble perfluorinated surface-active dispersing agents in CFC and perfluorinated propellants. These agents include perfluorinated sulfonamide alcohol phosphate esters and their salts, perfluorinated alkyl sulfonamide alkylene quaternary ammonium salts and perfluorinated alcohol phosphate esters and their salts. Thiel teaches that surfactants must be insoluble in the propellant. Further, he teaches that the drug must be coated with the surfactant in an organic solvent, dried, then added to the propellant mixture.

Johnson in U.S. Pat. No. 5,126,123 teaches aerosol inhalation drug formulations using propellant 134A and surfactants which include perfluoroalconic acid, potassium, perfluoroalkyl sulfonates and ammonium perfluoroalkyl carboxylates.

Johnson in U.S. Pat. No. 5,376,359 teaches methods of stabilizing an aerosol formulation containing solid dried particles. The surfactants used in these formulations include fluoropolymers that are soluble in the HFC propellant.

PCT WO 91/11173 teaches pressurized aerosol compositions containing a hydrofluorocarbon propellant and a fluorinated surfactant. Preferred surfactants include fluorinated alcohols, esters, amides, N-oxides or sulfonamides.

PCT WO 92/00061 teaches pressurized aerosol compositions containing a medicament, a hydrofluorocarbon propellant and a polyethoxylated surfactant. Preferred surfactants include non-fluorinated block copolymers of ethylene oxide and propylene oxide.

In the art, one disadvantage of incorporating a surfactant in an MDI formulation has been introducing the need for a corresponding co-solvent. In many situations, the presence of a co-solvent has one or more disadvantages. For example, the co-solvent may have toxicological issues. Moreover, while ethanol is basically safe, it is not suitable for all patient groups. Co-solvents may also have a higher Global Warming Potential (GWP) than the propellant somewhat negating one of the primary benefits of using HFC propellants. Co-solvents (e.g., ethanol) may dissolve the drug at elevated levels resulting in particle size growth at reduced levels. In other words, co-solvents (e.g., ethanol) may cause partial solubility of drug in suspension formulations, which can cause undesired particle growth through a process known in the art as "Ostwald Ripening." Such phenomena is very drug specific, however. Co-solvents may also lower the vapor pressure of the MDI formulation thereby reducing atomization performance, which adversely affects lung delivery performance. Such disadvantages may be exacerbated as the inhaler is operated because the concentration of co-solvent in the MDI formulation may increase.

The present invention is advantageous in that it overcomes the disadvantages discussed herein while imparting the advantages of employing the surfactants of the present invention in an MDI formulation. In the present invention, surfactants are employed without the need for a co-solvent.

SUMMARY OF THE INVENTION

The present invention, in one embodiment, relates to a pharmaceutical aerosol composition, comprising a drug, a fluorine-containing propellant, and an amphiphilic fluorinated block copolymer having at least one lyophobic block and at least one lyophilic block, wherein each of said blocks are formed from a plurality of monomeric units.

In another embodiment, the present invention relates to an aerosol composition, comprising particles, a fluorine-containing propellant, and an amphiphilic fluorinated block copolymer having at least one lyophobic block and at least one lyophilic block, wherein each of said blocks are formed from a plurality of monomeric units.

The present invention also relates to a pressurized container, such as a metered dose inhaler, containing the aerosol composition therein. The pressurized container preferably has a dispensing valve for dispensing the aerosol composition.

In a preferred embodiment of the invention, the amphiphilic fluorinated block copolymer comprises at least one lyophobic block, wherein the total molecular weight of the lyophobic block or blocks is between 500 and 5,000; and at least one lyophilic block, wherein the total molecular weight of the lyophilic block or blocks is between 3,000 and 30,000; and wherein each of said blocks are formed from a plurality of monomeric units; and wherein said fluorinated block copolymer is made from a lyophobic polymer which has a polydispersity index ($M_w/M_n$) of less than 1.5.

The invention further relates to an amphiphilic fluorinated block copolymer comprising at least one lyophobic block, wherein the total molecular weight of the lyophobic block or blocks is between 500 and 5,000; and at least one lyophilic block, wherein the total molecular weight of the lyophilic block or blocks is between 3,000 and 30,000; and wherein each of said blocks are formed from a plurality of monomeric units.

The present invention further relates to a method for improving the dispersability of a drug in an aerosol drug formulation, wherein the formulation comprises a fluorine-containing propellant and a medicament, comprising adding to the formulation an amphiphilic fluorinated copolymer having at least one lyophobic block and at least one lyophilic block, wherein each of said blocks are formed from a plurality of monomeric units.

The present invention further relates to a method for increasing the stability of an aerosol drug formulation, wherein the formulation comprises a fluorine-containing propellant and a medicament, comprising adding to the formulation an amphiphilic fluorinated copolymer having at least one lyophobic block and at least one lyophilic block, wherein each of said blocks are formed from a plurality of monomeric units.

The present invention also relates to a metered dose inhaler containing therein the pharmaceutical aerosol composition described above.

DETAILED DESCRIPTION OF THE INVENTION

Dispersability and Dosage

Contrary to popular belief and prior teachings, it is incorrect to state that the suspension should be uniform and free from large aggregates. The role of the surfactant is not to prevent aggregation but to control it and, thereby, influence the dispersability of the suspension.

The notion that the suspension should be non-aggregated would be true if it were possible to keep the drug particles in suspension indefinitely. However, the intrinsic density difference between the propellant and the drug particles means that phase separation of the suspension will occur; i.e., creaming or sedimentation of the particles will occur, depending on whether the drug material is less dense or more dense than the liquid, respectively. The rate of phase separation depends not only on the density difference but also on the size of the particles. Smaller particles will cream or sediment more slowly than larger ones. The slow creaming/sedimentation of individual (non-aggregated) particles leads to a tightly-packed layer of solid material that occupies a volume similar to the true volume of solid present. When aggregates of particles will cream or sediment more rapidly, the layer of solid formed will be much more loose and porous than the non-aggregated case. The aggregated material may have such a loose structure so as to appear to occupy a volume considerably greater than the true volume of solid.

Figure 4:
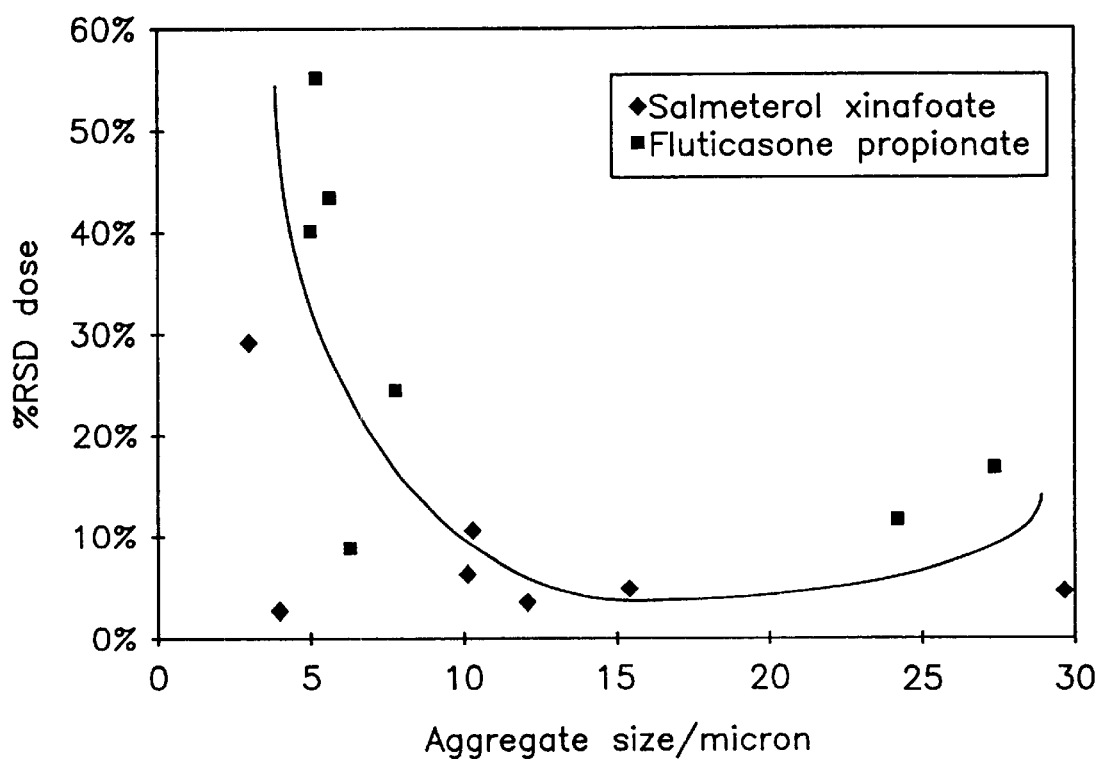
FIG. 4 is a graph illustrating the relationship between the dosing performance of the suspension and the aggregate size for Composition Examples 1–12 and a control suspension.

In the case of a creamed layer, it exists at a fluid interface and, as such, is readily disrupted by external agitation. A sedimented layer, on the other hand, sits at a rigid interface. For a tightly-packed sediment, significant external agitation may be required to remove the solid from the rigid interface. For a loosely-packed sediment, less external agitation is required. Therefore, the nature of the sediment can significantly influence the dispersability of the phase-separated formulation. This, in turn, strongly influences the homogeneity of the suspension. Clearly, in order to achieve consistent and uniform delivery of the solid material from the aerosol device, the metering valve must sample a homogeneous suspension. FIG. 4 illustrates the relationship between dosing performance and aggregate size for a sample of the present invention.

For conventional MDI systems, the sampling of the suspension occurs within a few seconds following actuation of the valve and emission of the previous dose. This sample may reside in the metering chamber for up to 16 hours in the case of those systems designed to be used by the patient twice-daily. For systems that need to be used on an "as needed" basis, the residence time in the metering chamber may be much longer. Unlike the bulk of suspension contained in the MDI reservoir, the suspension in the metering chamber does not co-exist with a vapor "head space" —i.e., the volume of the metering chamber is completely occupied by the liquid formulation. Phase separation of the contents of the metering chamber will occur as described earlier. Since there is no head space in the metering chamber, agitation (by external shaking) of the contents is very difficult to achieve. If a tightly-packed layer of particles has formed in the metering chamber, it may remain adhered to the interior surfaces of the chamber when the valve is actuated, resulting in a reduction of solid in the emitted dose. The influx of the next metered volume of formulation into the metering chamber may assist in the agitation of the adhered material remaining from the previous sample.

It is typical for a patient to actuate the MDI twice in order to receive the prescribed dose. Generally, the two actuations are made within a minute or so of each other. Therefore, the contents of the metering chamber sampled for the second actuation will have very little time to begin phase-separating. Since this second sample also contains solid material from the previous sample, the amount of solid in the emitted dose will be increased. This low-high dosing sequence will continue through-out the life of the inhaler, resulting in an erratic sawtooth-like dosing profile. In order to minimize the erratic nature of the dosing, it is important to control the aggregation behavior of the suspension such that it is not too aggregated to prevent uniform sampling from the bulk suspension but not insufficiently aggregated to lead to the phase separation problems described above.

It is well-known that the adsorption of appropriate surface active materials to the surface of the particles may be used to reduce the degree to which a dispersion will aggregate. The field of colloid science has taught that the extent to which aggregation is reduced depends, in part, on the length of the surfactant molecule. Quantitative theories exist that relate to this so-called steric stabilization, such as the combined theories of Deryaguin/Landau and Verwey/Overbeek (DLVO theory). The basic chemistry of the surfactant required is determined to a large extent by the chemical nature of the propellant and the bare particle surface. The size (molecular weight) of the surfactant required depends on many factors, including (but not limited to): particle size, particle-liquid density difference, liquid viscosity, overall system Hamaker constant, concentration of solid, metering valve geometry (including inlet orifice diameter and metering chamber volume) and the frequency at which the inhaler will be operated.

Surfactants/Block Copolymers

The surfactants useful in the present invention are amphiphilic fluorinated block copolymers comprising at least one lyophobic block and at least one lyophilic block. In the context of this invention, the term "amphiphilic" means that one or more portions of the copolymer have a thermodynamically favorable interaction with the liquid comprising the bulk phase of the formulation and that one or more portions of the copolymer have a thermodynamically unfavorable interaction with the liquid comprising the bulk.

Figure 1A:
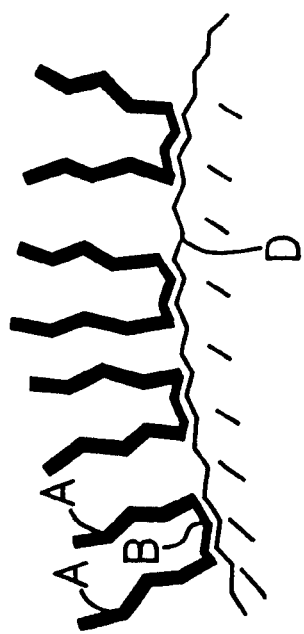
FIGS. 1A and 1B are schematic illustrations of the structure of ABA and AB block copolymers and their interactions with drug particles while in a solvent. Although the B block touches the drug particle, the figure has been drawn to more clearly distinguish the B block from the drug particle.
Figure 1B:
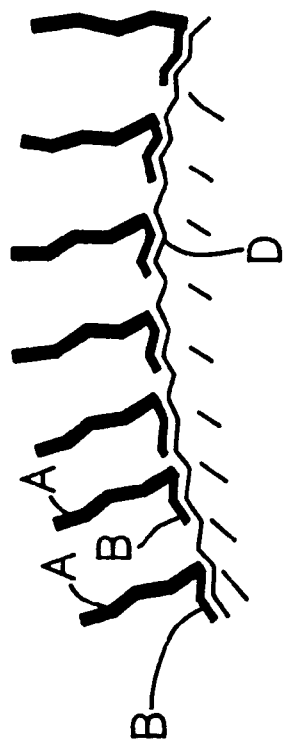

As illustrated in FIG. 1, the lyophobic portion of the surfactant, the "lyophobic anchor", has a thermodynamically favorable interaction with the particle, preferably a drug particle. The lyophilic portion of the surfactant, the "lyophilic tail", has a thermodynamically favorable interaction with the propellant in which the drug particles are dispersed.

The term "copolymer" means a molecule that is formed from two or more different monomers, portions, or repeating units. For example, a "lyophobic monomer" can be polymerized (or copolymerized with another monomer) to form a lyophobic block and a "lyophilic monomer" can be polymerized (or copolymerized with another monomer) to form a lyophilic block. The lyophobic and lyophilic blocks are connected to form a copolymer having at least one lyophobic block and at least one lyophilic block. The copolymer can be a linear (preferably with lyophilic and lyophobic side chains) or a branched copolymer and is preferably unbranched or linear. The individual blocks can be homopolymer blocks or copolymer blocks (either block or random). The copolymer can be a graft copolymer wherein one or more types of monomers are used to form a polymer or a copolymer and functional groups (either lyophobic or lyophilic groups) are introduced into the polymer by grafting to form the desired copolymer. In such a case, the polymer or copolymer onto which the functional groups are to be grafted should have appropriate reactive groups for introduction of the functional groups. In theory, the polymer would be both a block copolymer and a graft copolymer.

The block copolymer should have a soluble (lyophilic) block chain length long enough to prevent irreversible aggregation but not yield a level of aggregation low enough to cause erratic dosing via the mechanism caused above. The insoluble (lyophobic) block chain length should be long enough to adsorb well to the drug particle surface but not too long that it renders the overall polymer insoluble. A balance is required between the soluble and insoluble blocks.

The copolymer should preferably possess the following physical properties; (1) maintain a solubility in the propellant liquid in excess of 0.1% w/w across a temperature range from 5° C. to 40° C.; and (2) remain adsorbed at the propellant/drug interface across a temperature range from 5° C. to 40° C.

The lyophilic portion of the molecule has a high affinity for the solvent (or propellant). The lyophilic portion of the molecule is preferably formed from a monomer that contains one or more fluorine atoms, preferably five or more fluorine atoms, more preferably nine or more fluorine atoms and most preferably thirteen or more fluorine atoms. Various types of monomers are suitable for this portion of the molecule. Suitable monomers include, for example: (1) 1,1-dihydroperfluorooctyl acrylate/methacrylate (FOA/FOMA),
(2) 2-(N-ethylperfluoroalkylsulfonamido ethyl acrylate/methacrylate (FOSEA/FOSEMA), (3) Zonyl TA-N™.

The lyophilic portion (or lyophilic block in the case of a block copolymer) will usually have a side chain which contains carbon atoms and one or more fluorine atoms, preferably five or more fluorine atoms, more preferably nine or more fluorine atoms and most preferably thirteen or more fluorine atoms (depending on the type of monomer used in the polymerization). The carbon containing side chain may also have additional molecules such as oxygen atoms that may be present in the form of carbonyl (—O(C=O)—) groups, hydroxyl groups (—OH), etc. Preferably, the lyophilic blocks have a hydrocarbon portion in the backbone of the copolymer.

Figure 2:
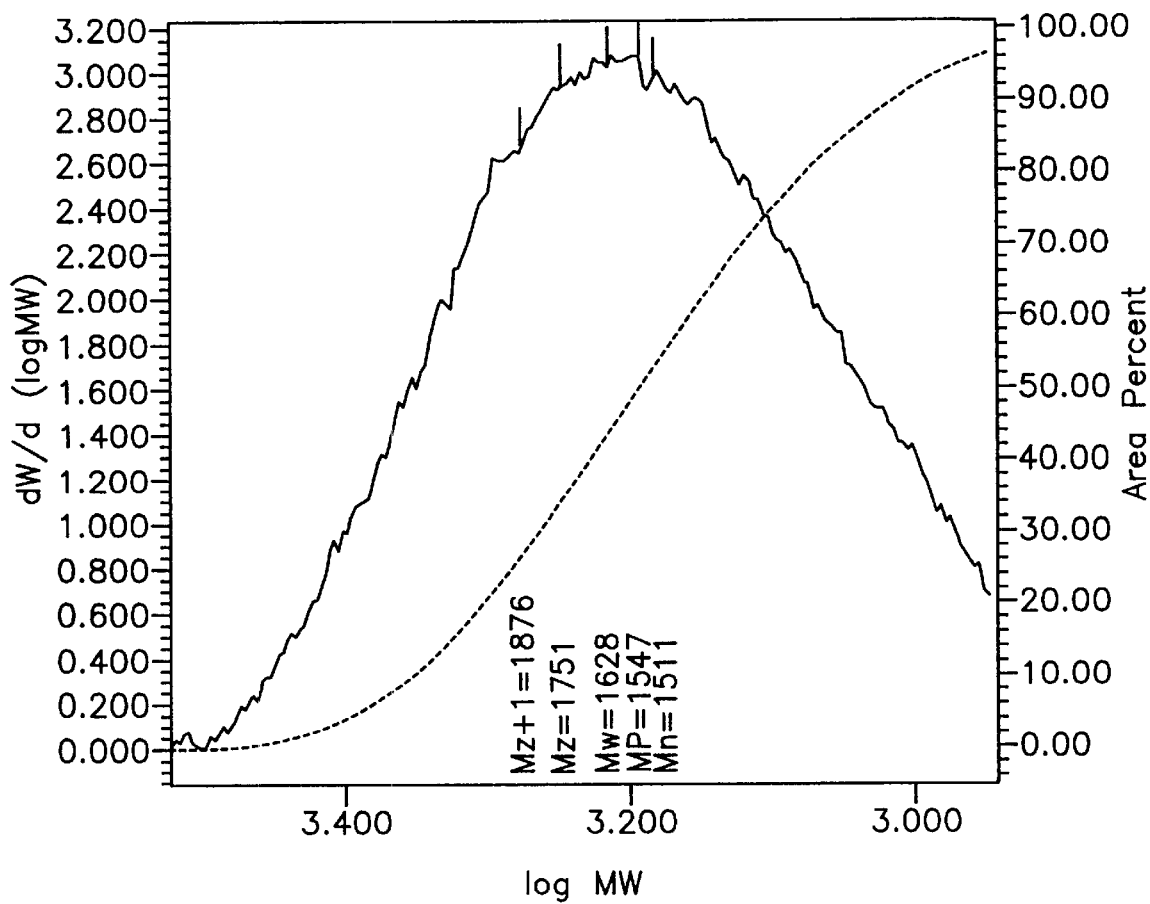
FIG. 2 shows the molecular weight distribution of a PHEA 1K polymer. The dashed line represents the cumulative distribution.
Figure 3:
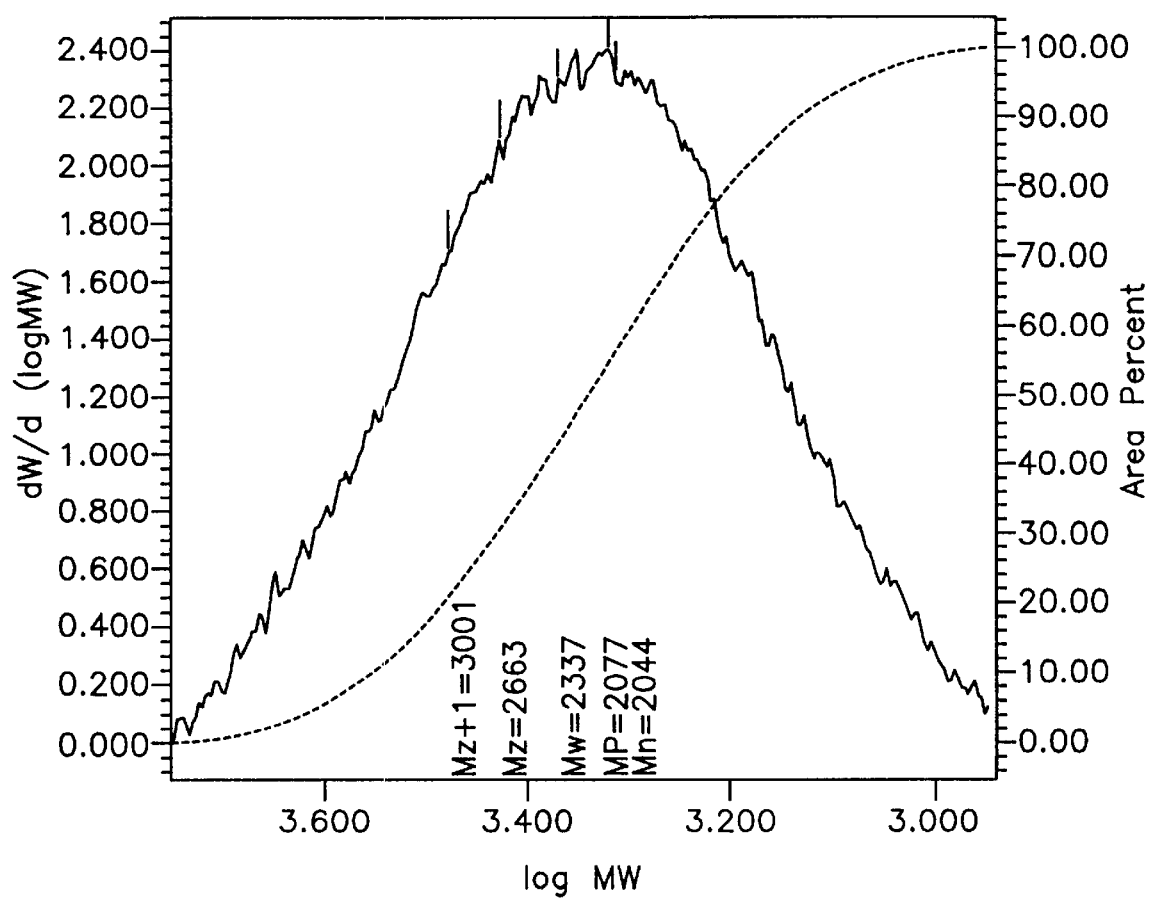
FIG. 3 shows the molecular weight distribution of a PHEA 2K polymer. The dashed line represents the cumulative distribution.

The lyophobic portion of the molecule has a low affinity for the solvent (or propellant). The lyophobic portion of the molecule is preferably formed from a monomer (or monomers) which contains less than 3 fluorine atoms, and preferably which does not contain any fluorine atoms. It is also preferred that the monomers do not contain any halogen atoms. Various types of monomers are suitable for this portion of the molecule. Suitable monomers include: styrene, vinyl acetate, hydroxyethyl acrylate, and dimethylaminoethyl methacrylate. FIGS. 2 and 3 illustrate the molecular weight distribution for PHEA of 1K and 2K polymers respectively.

In a preferred embodiment, the lyophobic portion of the molecule (or lyophobic blocks in the case of a block copolymer) are hydrocarbon blocks or hydrocarbon blocks containing one or more carbonyl groups. The lyophobic portion of the molecule will usually have a side chain which contains carbon atoms and no, or a small number of, fluorine atoms (depending on the type of monomer used in the polymerization). The carbon containing side chain, if present, may also have additional molecules such as oxygen atoms which may be present in the form of carbonyl (—O(C═O)—) groups, hydroxyl groups (—OH), etc. Other types of side chains or side groups include aromatic groups such as substituted or unsubstituted phenyl groups, ester groups (—C(═O)OR)or reverse ester (—OC(═O)R) groups wherein R is a lower alkyl group containing 1 to 6 carbon atoms, which can be optionally substituted with a hydroxyl group.

The copolymers of the present invention have repeating units which can be represented by the general formula $[a_n]_x[b_m]_y$ wherein a is a monomeric unit derived from a lyophilic monomer, b is a monomeric unit derived from a lyophobic monomer, n is an integer of 5 to 90, preferably 10 to 80, more preferably 15 to 80, most preferably 15 to 65, m is an integer of 5 to 30, preferably 6 to 20, more preferably 7 to 9, x is an integer of 1 or more, most preferably 1 or 2, y is an integer of 1 or more, usually 1 or 2, preferably 1. Representative block copolymers are AB, and ABA, wherein A is a lyophilic block (derived in whole or in part from lyophilic monomers) and B is a lyophobic block (derived in whole or in part from lyophobic monomers). Preferably, the block copolymer has a hydrocarbon copolymer backbone.

The block copolymer will usually have one or two lyophilic blocks and one lyophobic block. The total molecular weight of the lyophilic block(s) will typically be between 3000 and 30,000, preferably between 4000 and 20,000, more preferably between 5000 and 10,000. The molecular weight of the lyophobic block will usually be between 500 and 5000, preferably between 750 and 3000, more preferably between 1000 and 2000. The preferred actual molecular weight of each block will depend on a number of factors as discussed above. The polydispersity index ($M_w/M_n$) of the lyophobic block (the lyophobic polymer used to prepare the block copolymer) is usually less than 1.5, preferably less than 1.3, more preferably less than 1.2. In a preferred embodiment, the lyophobic block is a hydrocarbon block, and the lyophilic block is derived from a fluorocarbon acrylate or methacrylate monomer.

The block copolymers are added in an amount sufficient to improve the performance of the aerosol formulation in at least one relevant property, described above, as compared to a formulation not containing any block copolymer. In pharmaceutical formulations, the copolymer to drug weight ratio is usually 0.01 to 2.0:1, preferably 0.01 to 0.25:1, most preferably 0.02 to 0.05:1

The structures of the repeating units of several representative copolymers that are useful in accordance with the present invention are illustrated below.

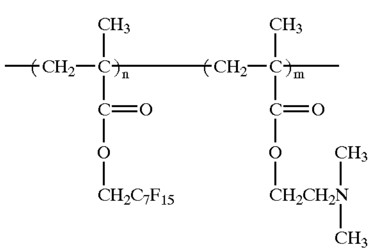

PFOMA-b-PDMAEMA

-continued

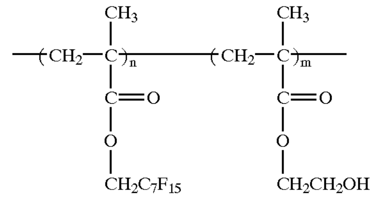

PFOMA-b-PHEMA

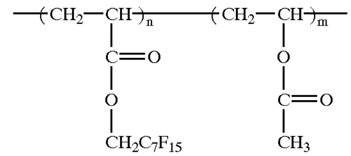

PFOA-b-PVAc

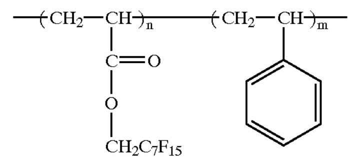

PFOA-b-PS

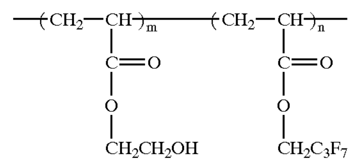

PHEA-b-PFBA

Abbreviations

HEA = 2-hydroxyethyl acrylate
FOA = fluorinated octylacrylate
PFOA = polyfluorinated octylacrylate
PS = polystyrene
PVAc = polyvinylacetate
VAc = vinylacetate
PDMAEMA = poly(dimethylaminoethyl methacrylate)
PHEMA = polyhydroxy ethyl methacrylate
PFOMA = polyfluoro octyl methacrylate
PHEA-b-PFOMA = poly(hydroxy ethyl acrylate-b-fluoro octyl methacrylate)
PFBA = polyfluoro butyl acrylate

Propellants

"Propellants" used herein mean pharmacologically inert liquids with boiling points from about room temperature (25° C.) to about −25° C. that singly or in combination exert a high vapor pressure at room temperature. The vapor pressure should be on the order of 5 to 10 bar, allowing significant potential energy to be available for atomization. Such propellants include fluorine-containing propellants, more preferably non-CFCs, and most preferably hydrofluorocarbons. The propellants used in the present invention are low boiling fluorine-containing propellants; in particular, hydrofluorocarbons or hydrofluoroalkanes such as HFC-134a and HFC-227. The invention is particularly useful with propellants (including propellant mixtures) which are more hygroscopic than P11 (trichlorofluoromethane), P114 (1,2-dichlorotetrafluoroethane) and/or P12 (dichlorodifluoromethane) such as HFC-134a and HFC-227 and mixtures thereof, preferably HFC-134a.

After considering the amount of drug and copolymer (and other optional ingredients), the propellant will make up the remainder of the composition. Propellants are typically included in the aerosol compositions of the present invention in an amount of at least about 95% by weight of the total weight of the composition preferably in an amount of at least about 99% by weight of the total weight of the composition.

Drugs

Drugs useful in this invention should be in solid particulate form typically with a mass median aerodynamic diameter under 20 microns, preferably between 0.5 and 10 microns and even more preferably between 1 and 5 microns. Drugs, or medicaments, appropriate for this invention include those drugs adaptable to inhalation administration, for example, antiallergenic, respiratory (e.g., antiasthmatic and bronchodilating), antibiotic, anti-inflammatory, antifungal, analgesic, antiviral, and cardiovascular drugs. Where appropriate, the drugs may be used in the form of salts (e.g., as alkali metal or amine salts or as acid addition salts), or as esters (e.g. as lower alkyl esters). Preferred drugs and drug combinations are disclosed in WO 96/32151, WO 96/32345, WO 96/32150 and WO 96/32099, the entire contents of which are hereby incorporated by reference. These drugs include, for example, fluticasone propionate or a physiologically acceptable solvate thereof, beclomethasone dipropionate or a physiologically acceptable solvate tulobuterol, orciprenaline, 4-hydroxy-7-[2-[[2-[[3-(2-phenylethoxy)propyl]sulfonyl]ethyl]amino]ethyl-2(3H)-benzothiazolone, or (−)-4-amino-3,5-dichloro-α-[[[6-[2-(2-pyridinyl)ethoxy]hexyl]-amino]methyl]benzene-methanol; diuretics, e.g., amiloride; anticholinergics e.g., tiotropium, ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament and/or to minimize the solubility of the medicament in the propellant.

The drug is typically included in the aerosol compositions of the present invention in an amount of at least about 0.01% by weight of the total weight of the composition, preferably in an amount of between 0.02 and 0.5% by weight of the total weight of the composition.

The structures of several drugs useful in the invention are illustrated below.

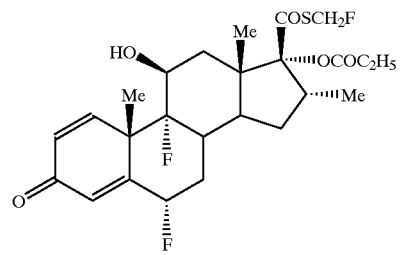

Fluticasone Propionate

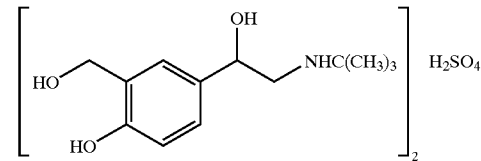

Albuterol Sulfate

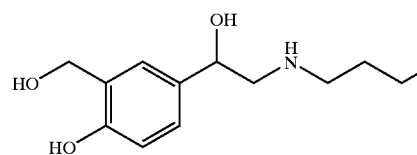

Salmeterol Hydroxynaphthoate

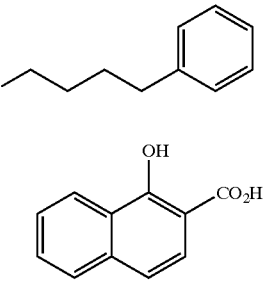

thereof, salmeterol or a physiologically acceptable salt thereof and albuterol or a physiologically acceptable salt thereof. Medicaments may be selected from, for example, analgesics, e.g. codeine, dihydromorphine, ergotamine, fentanyl or morphine, anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g. mometasone (e.g. the furoate), rofleponide, fluticasone propionate, beclomethasone (e.g., the dipropionate), flunisolide, budesonide, tipredane or triamcinolone acetonide; antitussives, e.g., noscapine; bronchodilators, e.g., albuterol (or salbutamol), salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, Salmeterol hydroxynaphthoate is also known as salmeterol xinafoate. Albuterol sulphate is also known as salbutamol sulphate. Additionally, any suitable combination of drugs can be used in the present invention. For example, the combination of drugs used in Seretide™ (fluticasone propionate and salmeterol hydroxynaphthoate) can be used in the present invention.

Optional Excipients

It may be desirable to add other excipients to an aerosol formulation to improve drug delivery, shelf life and patient acceptance. Such optional excipients include, but are not limited to, bulking agents (e.g. lactose), co-solvents (e.g. ethanol), taste masking agents, antioxidants and chemical stabilizers.

Pressurized Containers

The pressurized containers useful in the invention include any containers in which a drug and a propellant can be stored. The pressurized container is preferably an MDI or an MDI can. The term "metered dose inhaler" or "MDI" means a unit comprising a can, a cap secured to the can (e.g. via ultrasonic welding, screw fitting, crimping) providing an air-tight seal and covering the mouth of the can, and a drug metering valve situated in the cap, while the term "MDI system" also includes a suitable channeling device. The term "MDI can" means the container without the cap and valve. The term "drug metering valve" or "MDI valve" refers to a valve and its associated mechanisms which delivers a predetermined amount of drug formulation from an MDI upon each activation. The channeling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538 incorporated herein by reference. A suitable MDI is disclosed in WO 96/26755, the entire contents of which is hereby incorporated by reference. Preferred pressurized containers for use in MDIs are disclosed in WO 96/32151, WO 96/32345, WO 96/32150 and WO 96/32099.

The pressurized container is preferably a vial made from aluminum. However, other materials are not beyond the scope of the present invention. Other materials for the pressurized container include, but are not limited to, ferrous alloys, non-ferrous alloys, ceramic materials, polymers, composite materials, and mixtures thereof. Suitable containers that contain a polymeric coating on the inside thereof are disclosed in WO 96/32151.

EXAMPLES

General Surfactant Synthesis 1H, 1H-Heptafluorobutyl acrylate was obtained from Oakwood Research Chemicals and purified by passing through an alumina column. HEA was obtained from Aldrich and the hydroxy functionality was protected using trimethylsilyl chloride (TMS). HEMA was obtained from Aldrich in the hydroxy-protected form: (2-trimethylsilyloxy)ethyl methacrylate. The hydroxy functionality is regenerated using tetrabutyl ammonium fluoride. All polymerizations were conducted in 25–50 ml round bottom flasks. In the synthesis examples, an AB copolymer was produced.

The molecular weight (MW) of the final block copolymer is equal to the MW of the lyophilic block plus the MW of the lyophobic block. The MW of the lyophobic block is determined by GPC. The MW of the lyophilic block can be determined be two methods. In the first method, the theoretical MW of the lyophilic polymer is multiplied by the gravimetric conversion. In the second method, proton NMR is used, whereby if the MW of the lyophobic blocK is known, a ratio of integrated peak areas from the NMR spectrum of the block copolymer allows the calculation of the lyophilic block.

Synthesis Example 1
PHEA-b-PFBA

A representative example is as follows. A flask was charged with CuBr (1.5 mmol) and purged with a flow of argon for at least 15 minutes. A degassed solution of HEA (16 mmol), wherein the hydroxy group is protected with TMS, methyl-2-bromopropionate (1.5 mmol) and pentamethyldiethylene triamine (1.5 mmol) was added using a cannula under an argon pressure. The amount of methyl-2-bromopropionate was varied to provide PHEA blocks of various sizes, as shown in Table 1. The reaction proceeded for 45 min. at 80° C. Upon completion, an NMR was taken of the solution to determine the final conversion and the polymer was dissolved in acetone and passed through an alumina column for removal of copper. Residual solvent was removed under vacuum. The PHEA polymer was then characterized by gel permeation chromatography (GPC) for molecular weight and polydispersity information (See FIGS. 2 and 3).

The synthesis of the block copolymer was performed in a similar manner as the PHEA polymer above, with the exception that the HEA monomer was replaced with 1H, 1H-heptafluorobutyl acrylate (39.4 mmol), and the methyl-2-bromopropionate was replaced with PHEA (0.224 mmol). Trifluorotoluene (TFT) (10 ml) was used as the solvent medium and pentamethyldiethylene triamine was replaced with bipyridine (0.100 mmol) . When the reaction was complete, an NMR was taken and the polymer solution was diluted with additional TFT, passed through an alumina column and precipitated into tetrahydrofuran (THF) containing tetrabutyl ammonium fluoride. The polymer was then collected by vacuum filtration over a Hirsch funnel. For further purification, the polymer was placed in a soxhlet extractor with THF, followed by methanol.

TABLE 1

| Polymer ID | MW of PHEA block | MW of PFBA block | No. of HEA monomer units (m) | No. of PFBA monomer units (n) |
| --- | --- | --- | --- | --- |
| 1K/5K  | 1K | 5K  | 9  | 15 |
| 1K/10K | 1K | 10K | 9  | 31 |
| 1K/20K | 1K | 20K | 9  | 62 |
| 2K/5K  | 2K | 5K  | 17 | 15 |
| 2K/10K | 2K | 10K | 17 | 31 |
| 2K/20K | 2K | 20K | 17 | 62 |

FIGS. 2 and 3 illustrate the molecular weight distribution of the PHEA 1K and 2K polymers respectively. The PHEA 1K polymer had a MW of 1628 Daltons and a polydispersity index of 1.077093. The PHEA 2K polymer had a MW of 2337 Daltons and a polydispersity index of 1.143430.

Syntesis Example 2
PS-b-FOA

A typical polymerization is as follows. Into a round bottom flask, equipped with a stir bar, was added tetraethylthiuramdisulfide (TD) and styrene monomer. The flask was then sealed with a septum and purged with argon. After purging, the flask was wrapped in aluminum foil to keep out unwanted light, and was placed into a constant temperature bath at 65–85° C. for 9–15 h. The polymer was isolated by precipitation into a large excess of methanol. The polymer (TD-PS) was then collected by suction filtration and dried under vacuum. The polymer was purified twice by redissolving the polymer in tetrahydrofuran and precipitating into methanol.

The diblock copolymer was synthesized by the subsequent polymerization of FOA using TD-PS as the macroiniferter. Polymerizations were conducted in trifluorotoluene (TFT) as the solvent. The polymerizations were initially cloudy but became clear as the polymerization proceeded. A typical experimental procedure is described as follows. Into a quartz flask equipped with a stir bar was added the TD-PS sample. The polymer was then dissolved in TFT. FOA monomer was added and the flask was sealed with a septum and purged with argon. In some cases, the FOA monomer was added to the TD-PS solution until a cloudy solution persisted, the rest of the monomer was then syringed into the solution over the course of the polymerization to prevent precipitation of the TD-PS macroiniferter. After purging with argon, the solution was photolyzed at room temperature with stirring for 30 h in a sixteen-bulb Rayonet photoreactor equipped with 350 nm bulbs. The polymer was then collected by precipitation into a large excess of cyclohexane and dried under vacuum. The block copolymer was purified by Soxhlet extraction using cyclohexane for approximately 2 days to remove any unreacted PS homopolymer and block copolymer that was low in fluorocarbon incorporation.

Synthesis Example 3

PVAc-b-FOA

A typical polymerization is as follows. Into a quartz flask equipped with a stir bar was added vinyl acetate (VAc), benzyl N,N-diethyldithiocarbamate (BDC) and TD. The flask was then sealed with a septum and purged with argon. The solution was photolyzed at room temperature with stirring for 30 h in a sixteen-bulb Rayonet photoreactor equipped with 350 nm wavelength bulbs. The polymer was then collected by precipitation into a large excess of heptane and dried under vacuum. The resulting polymer was purified twice by dissolution in acetone followed by reprecipitation into heptane.

The PVAc diblock copolymer was synthesized by the subsequent polymerization of FOA using BDC-PVAc as the macroiniferter. Polymerizations were conducted in TFT solution. The polymerization was clear and homogeneous throughout the polymerization. Initially, a quartz flask was equipped with a stir bar and BDC-PVAc was added. The polymer was then dissolved in TFT. FOA monomer was added and the flask was sealed with a septum and purged with argon. After purging, the solution was photolyzed at room temperature with stirring for 30 h in a sixteen bulb Rayonet photoreactor equipped with 350 nm bulbs. The polymer was then collected by precipitation into a large excess of methanol and dried under vacuum. The block copolymer was purified by Soxhlet extraction using methanol for approximately 2 days to remove any unreacted PVAc homopolymer.

Synthesis Example 4

PDMAEMA-b-FOMA

A typical polymerization is as follows. Into a quartz flask equipped with a stir bar was added dimethyl aminomethacrylate (DMAEMA), benzyl N,N-diethyldithiocarbamate (BDC) and TD. The flask was then sealed with a septum and purged with argon. The solution was photolyzed at room temperature with stirring for 30 h in a sixteen-bulb Rayonet photoreactor equipped with 350 nm wavelength bulbs. The polymer was then collected by precipitation into a large excess of hexane and dried under vacuum. The resulting polymer was purified twice by dissolution in tetrahydrofuran followed by reprecipitation into heptane.

The PDMAEMA diblock copolymer was synthesized by the subsequent polymerization of FOMA using BDC-PDMAEMA as the macroiniferter. Polymerizations were conducted in TFT solution. The polymerization was clear and homogeneous throughout the polymerization. Initially, a quartz flask was equipped with a stir bar and BDC-PDMAEMA was added. The polymer was then dissolved in TFT. FOMA monomer was added and the flask was sealed with a septum and purged with argon. After purging, the solution was photolyzed at room temperature with stirring for 30 h in a sixteen bulb Rayonet photoreactor equipped with 350 nm bulbs. The polymer was then collected by precipitation into a large excess of hexanes and dried under vacuum. The block copolymer was purified by Soxhlet extraction using methanol for approximately 2 days to remove any unreacted PDMAEMA homopolymer.

Synthesis Example 5

PFOMA-b-PHEMA

A representative example is as follows. The flask was charged with CuBr (1.5 mmol) and bipyridine (0.100 mmol) and purged with a flow of argon for at least 15 minutes. A degassed solution of HEMA (16 mmol), wherein the hydroxy group is protected with TMS, and methyl-2-bromopropionate (1.5 mmol) was added using a cannula under argon under pressure. The amount of methyl-2-bromopropionate was varied to provide PHEMA blocks of various sizes. The react-on proceeded for 45 min. at 80° C. Upon completion, an NMR was taken of the solution to determine the final conversion and the polymer was dissolved in acetone and passed through an alumina column for removal of copper. Residual solvent was removed under vacuum. The polymer was then characterized by GPC for molecular weight information. The synthesis of the block copolymer was performed in a similar manner to the HEMA polymerization described above, with the exception that the HEMA monomer was replaced with 1H, 1H-perfluorooctyl methacrylate (39.4 mmol), and the methyl-2-bromopropionate was replaced with PHEMA (0.224 mmol). TFT (10 ml) was used as the solvent medium. When the reaction was complete, an NMR was taken and the polymer solution was diluted with additional TFT, passed through an alumina column and precipitated into tetrahydrofuran (THF) containing tetrabutyl ammonium fluoride. The polymer was then collected by vacuum filtration over a Hirsch funnel. For further purification, the polymer was placed in a soxhlet extractor with THF, followed by methanol.

Composition Preparation

The compositions were prepared as follows:

Composition Example 1

Micronized salmeterol hydroxynaphthoate (88 mg) and polymer ID 1K/5K from Table 1 (4.4 mg) were weighed into a 15 ml transparent glass aerosol vial and a metering valve was crimped into place. 1,1,1,2-tetrafluoroethane (P134a, 12 g) was added to the vial through the valve. The vial was sonicated for 30 seconds to aid dispersion of the drug and the surfactant.

Composition Examples 2–24

Using the procedure described in Composition Example 1, the following formulations were prepared:

TABLE 2

| Example | Drug (mass) | Compound from Table 1 (mass) |
|---|---|---|
| 2 | Salmeterol hydroxynaphthoate (88 mg) | 1K/10K (4.4 mg) |
| 3 | Salmeterol hydroxynaphthoate (88 mg) | 1K/20K (4.4 mg) |
| 4 | Salmeterol hydroxynaphthoate (88 mg) | 2K/5K (4.4 mg) |
| 5 | Salmeterol hydroxynaphthoate (88 mg) | 2K/10K (4.4 mg) |

TABLE 2-continued

| Example | Drug (mass) | Compound from Table 1 (mass) |
|---|---|---|
| 6 | Salmeterol hydroxynaphthoate (88 mg) | 2K/20K (4.4 mg) |
| 7 | Fluticasone propionate (60 mg) | 1K/5K (3 mg) |
| 8 | Fluticasone propionate (60 mg) | 1K/10K (3 mg) |
| 9 | Fluticasone propionate (60 mg) | 1K/20K (3 mg) |
| 10 | Fluticasone propionate (60 mg) | 2K/5K (3 mg) |
| 11 | Fluticasone propionate (60 mg) | 2K/10K (3 mg) |
| 12 | Fluticasone propionate (60 mg) | 2K/20K (3 mg) |
| 13 | Albuterol base (60 mg) | 1K/5K (3 mg) |
| 14 | Albuterol base (60 mg) | 1K/10K (3 mg) |
| 15 | Albuterol base (60 mg) | 1K/20K (3 mg) |
| 16 | Albuterol base (60 mg) | 2K/5K (3 mg) |
| 17 | Albuterol base (60 mg) | 2K/10K (3 mg) |
| 18 | Albuterol base (60 mg) | 2K/20K (3 mg) |
| 19 | Albuterol sulfate (72 mg) | 1K/5K (3.6 mg) |
| 20 | Albuterol sulfate (72 mg) | 1K/10K (3.6 mg) |
| 21 | Albuterol sulfate (72 mg) | 1K/20K (3.6 mg) |
| 22 | Albuterol sulfate (72 mg) | 2K/5K (3.6 mg) |
| 23 | Albuterol sulfate (72 mg) | 2K/10K (3.6 mg) |
| 24 | Albuterol sulfate (72 mg) | 2K/20K (3.6 mg) |

Composition Example 25

Polymer ID 1K/10K from Table 1 (13.9 mg) was weighed into a 12.5 ml aluminum aerosol can and a metering valve was crimped into place. 1,1,1,2-tetrafluoroethane (P134a, 18 g) was added to the vial through the valve. The vial was sonicated for 30 seconds to aid dissolution of the surfactant. One metered actuation of this solution was fired into an empty 8 ml aluminum aerosol can so as to dispense a total of 0.058 mg of surfactant into the aerosol can. Following complete evaporation of the residual propellant, a metering valve was crimped into place. Meanwhile, micronized salmeterol hydroxynaphthoate (2.91 g) was added to a charge vessel and liquefied 1,1,1,2-tetrafluoroethane (P134a, 6.91 kg) was pressure filled through the charge vessel into a manufacturing vessel. The drug suspension was mixed thoroughly and a 12 g aliquot of the suspension was filled into the can/valve combination described above containing the surfactant. The inhaler device containing the propellant, drug and surfactant was sonicated for 30 seconds to aid dissolution of the surfactant and thorough mixing with the drug. The final composition of the inhaler device was:

Propellant: 12 g

Drug substance: 5.8 mg

Surfactant: 0.058 mg

Composition Examples 26–28

Using the procedure described in Example 25, the following formulations were prepared:

TABLE 3

| Example | Drug (mass) | Compound from Table 1 (mass) |
|---|---|---|
| 26 | Salmeterol hydroxynaphthoate (5.8 mg) | 1K/10K (0.58 mg) |
| 27 | Salmeterol hydroxynaphthoate (5.8 mg) | 2K/20K (0.058 mg) |
| 28 | Salmeterol hydroxynaphthoate (5.8 mg) | 2K/20K (0.58 mg) |

Composition Characterization

In Tables 4 and 5, the suspensions containing Composition Examples 1–12 were characterized by a laser back scattering technique (Lasentec Labtec 1000) to determine the mean aggregate size of the particles in the suspension. Four such measurements were taken over a period of 21 days. The dosing performance for each composition was determined by collecting 14 doses from the inhaler device and quantifying the amount of drug emitted using a chromatographic analytical method. The results are given in Tables 4 and 5 for salmeterol hydroxynaphthoate and fluticasone propionate suspensions, respectively. The dosing performance is represented by the relative standard deviation of the 14 doses collected. By way of comparison, results are also presented for a control suspension of equivalent composition but with no surfactant present (designated Control).

TABLE 4

Salmeterol Hydroxynaphthoate

| Composition | Aggregate size/μm | | | | | % RSD for |
|---|---|---|---|---|---|---|
| Example | Day 0 | Day 7 | Day 14 | Day 21 | Mean/μm | dose |
| Control | 27.9 | 31.9 | 28.1 | 31.3 | 29.8 | 4.6% |
| 1 | 2.7 | 6.0 | 4.8 | 2.6 | 4.0 | 2.7% |
| 2 | 14.4 | 20.6 | 12.1 | 14.6 | 15.4 | 4.9% |
| 3 | 15.7 | 11.3 | 11.6 | 10.0 | 12.1 | 3.5% |
| 4 | 11.7 | 8.6 | 10.5 | 10.0 | 10.2 | 6.3% |
| 5 | 11.9 | 10.9 | 10.2 | 8.3 | 10.3 | 10.6% |
| 6 | 2.2 | 3.2 | 3.4 | 3.1 | 3.0 | 29.1% |

TABLE 5

Fluticasone Propionate

| Composition | Aggregate size/μm | | | | | % RSD for |
|---|---|---|---|---|---|---|
| Example | Day 0 | Day 7 | Day 14 | Day 21 | Mean/μm | dose |
| Control | 20.9 | 25.0 | 33.9 | 29.5 | 27.3 | 16.6% |
| 7 | 7.8 | 5.4 | 4.2 | 5.1 | 5.6 | 43.2% |
| 8 | 26.7 | 26.9 | 21.3 | 21.7 | 24.2 | 11.5% |
| 9 | 5.1 | 6.0 | 6.1 | 7.9 | 6.3 | 8.7% |
| 10 | 2.5 | 5.4 | 5.6 | 6.5 | 5.0 | 40.1% |
| 11 | 7.9 | 8.3 | 8.5 | 6.4 | 7.8 | 24.3% |
| 12 | 5.7 | 5.0 | 4.8 | 5.1 | 5.2 | 55% |

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

We claim:

1. A pharmaceutical aerosol composition, comprising:
   a drug;
   a fluorine-containing propellant; and
   an amphiphilic fluorinated block copolymer having at least one lyophobic block and at least one lyophilic block, wherein each of said blocks are formed from a plurality of monomeric units.

2. The composition of claim 1, wherein said amphiphilic fluorinated block copolymer comprises at least one lyophobic block, wherein the total molecular weight of the lyophobic block or blocks is between 500 and 5,000; and at least one lyophilic block, wherein the total molecular weight of the lyophilic block or blocks is between 3,000 and 30,000; and wherein each of said blocks are formed from a plurality of monomeric units; and wherein said fluorinated block copolymer is made from a lyophobic polymer which has a polydispersity index of less than 1.5.

3. The composition of claim 1, wherein said lyophobic blocks are hydrocarbon blocks or hydrocarbon blocks containing one or more carbonyl groups.

4. The composition of claim 1, wherein said lyophilic blocks have a fluorinated side chain.

5. The composition of claim 4, wherein said lyophilic blocks have a hydrocarbon portion in the backbone of said copolymer.

6. The composition of claim 1, wherein said copolymer has a hydrocarbon copolymer backbone.

7. The composition of claim 1, wherein the lyophobic block is a hydrocarbon block and the lyophilic block is derived from a fluorocarbon acrylate monomer.

8. The composition of claim 1, wherein the drug is an antiallergenic, respiratory, antibiotic, anti-inflammatory, antifungal, analgesic, antiviral or cardiovascular drug.

9. The composition of claim 1, wherein the drug is selected from the group consisting of fluticasone propionate, albuterol sulphate, and salmeterol hydroxynaphthoate or a pharmaceutically acceptable salt or solvate thereof.

10. The composition of claim 1, wherein the fluorine-containing propellant is 1,1,1,2-tetrafluoroethene or 1,1,1,2,3,3,3-heptafluoropropane.

11. The composition of claim 1, wherein the copolymer to drug weight ratio is 0.01–2.0:1.

12. The composition of claim 1, wherein the copolymer to drug weight ratio is 0.1 to 0.25:1.

13. A metered dose inhaler containing therein the composition of claim 1.

14. A method for improving the dispersability of a drug in an aerosol drug formulation, wherein the formulation comprises a fluorine-containing propellant and a medicament, comprising:

adding to the formulation an amphiphilic fluorinated copolymer having at least one lyophobic block and at least one lyophilic block, wherein each of said blocks are formed from a plurality of monomeric units.

15. The method of claim 14, wherein the fluorine-containing propellant is selected from 1,1,1,2-tetrafluoroethene or 1,1,1,2,3,3,3-heptafluoropropane.

16. A method for increasing the stability of an aerosol drug formulation, wherein the formulation comprises a fluorine-containing propellant and a medicament, comprising:

adding to the formulation an amphiphilic fluorinated copolymer having at least one lyophobic block and at least one lyophilic block, wherein each of said blocks are formed from a plurality of monomeric units.

* * * * *

UNITED STATES PATENT AND TRADEMARK OFFICE
CERTIFICATE OF CORRECTION

PATENT NO. : 6,451,287 B1
DATED : September 17, 2002
INVENTOR(S) : Joseph M. Desimone et al.

It is certified that error appears in the above-identified patent and that said Letters Patent is hereby corrected as shown below:

<u>Title page,</u>
Item [73], Assignee, add -- University of North Carolina (US) --.

Signed and Sealed this

Fourteenth Day of December, 2004

JON W. DUDAS
*Director of the United States Patent and Trademark Office*